(12) United States Patent
Ottosen

(10) Patent No.: US 6,750,253 B1
(45) Date of Patent: Jun. 15, 2004

(54) AMINOBENZOPHENONES AS INHIBITORS OF IL-1β AND TNF-α

(75) Inventor: Erik Rytter Ottosen, Ølstykke (DK)

(73) Assignee: Leo Pharmaceutical Products Ltd. A/S, Ballerup (DK)

( * ) Notice: Subject to any disclaimer, the term of this patent is extended or adjusted under 35 U.S.C. 154(b) by 128 days.

(21) Appl. No.: 10/030,970

(22) PCT Filed: Jul. 11, 2000

(86) PCT No.: PCT/DK00/00387

§ 371 (c)(1),
(2), (4) Date: Feb. 22, 2002

(87) PCT Pub. No.: WO01/05751

PCT Pub. Date: Jan. 25, 2001

Related U.S. Application Data

(60) Provisional application No. 60/144,062, filed on Jul. 16, 1999.

(51) Int. Cl.⁷ .................... A61K 31/17; C07C 275/28
(52) U.S. Cl. .................. 514/596; 564/48; 564/50; 562/561; 560/169; 514/597; 514/592; 514/578; 514/557; 514/551
(58) Field of Search ............... 514/596, 597, 514/592, 578, 557, 551; 564/48, 50; 562/561; 560/169

(56) References Cited

FOREIGN PATENT DOCUMENTS

WO          98/32730          7/1998

*Primary Examiner*—Charanjit S. Aulakh
(74) *Attorney, Agent, or Firm*—Birch, Stewart Kolasch & Birch, LLP

(57) ABSTRACT

The present invention relates to compounds of the formula

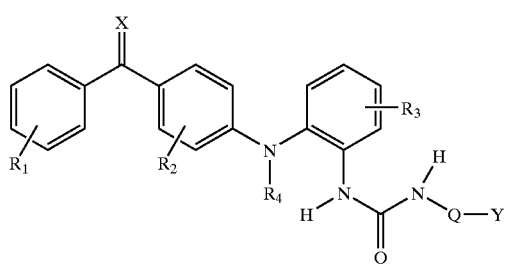

I wherein $R_1$ independently represents one or more, same or different substituents selected from the group consisting of halogen, hydroxy, mercapto, trifluoromethyl, amino, $(C_1-C_3)$alkyl, $(C_2-C_3)$olefinic group, $(C_1-C_3)$alkoxy, $(C_1-C_3)$alkylthio, $(C_1-C_6)$alkylamino, $(C_1-C_3)$alkoxycarbonyl, cyano, carbamoyl, phenyl and nitro, provided that when $R_1$ represents one substituent, it is in the ortho position, and when $R_1$ represents more than one substituent, at least one $R_1$ substituent is in the ortho position; $R_2$ is one substituent in the ortho position, said substituent being selected from the group consisting of hydrogen, halogen, hydroxy, mercapto, trifluoromethyl, amino, $(C_1-C_3)$alkyl, $(C_2-C_3)$olefinic group, $(C_1-C_3)$alkoxy, $(C_1-C_3)$alkylthio, $(C_1-C_6)$alkylamino, $(C_1-C_3)$alkoxycarbonyl, cyano, carbamoyl, phenyl and nitro; $R_3$ represents hydrogen, halogen, hydroxy, mercapto, trifluoromethyl, amino, $(C_1-C_3)$alkyl, $(C_2-C_3)$olefinic group, $(C_1-C_3)$alkoxy, $(C_1-C_3)$alkylthio, $(C_1-C_6)$alkylamino, $(C_1-C_3)$alkoxycarbonyl, phenyl, cyano, carboxy, or carbamoyl; $R_4$ represents hydrogen, $(C_1-C_3)$alkyl, or allyl. The compounds are valuable in the human and veterinary therapy.

14 Claims, No Drawings

AMINOBENZOPHENONES AS INHIBITORS OF IL-1β AND TNF-α

This application is the national phase under 35 U.S.C. §371 of PCT International Application No. PCT/DK00/00387 now WO 01/05751 which has an International filing date of Jul. 11, 2000, which designated the United States of America and was published in English which claims benefit of 60/144,062 filed Jul. 16, 1999.

FIELD INVENTION

This invention relates to a hitherto unknown class of compounds which shows anti-inflammatory effects, to pharmaceutical preparations containing these compounds, to dosage units of such preparations, and to their use in the treatment and prophylaxis of asthma, allergy, arthritis, including rheumatoid arthritis and spondyloarthritis, gout, atherosclerosis, chronic inflammatory bowel disease (Crohn's disease), proliferative and Inflammatory skin disorders, such as psoriasis and atopic dermatitis, uveitis, septic shock, AIDS, and acne.

BACKGROUND OF THE INVENTION

Previously, a series of closely related aminobenzophenones (e.g. 4-(2-amino-4-nitrophenylamino)benzophenone) have been described (Hussein, F. A. et al, Iraqi J. Sci., 22, 54–66 (1981)). However, there Is no description of their uses. PCT/DK98/00008 discloses aminobenzophenone inhibitors of interleukin 1β (IL-1β) and tumour necrosis factor α (TNF-α) secretion in vitro, said compounds being potentially useful for treatment of inflammatory diseases in which the production of cytokines is involved In the patho-genesis, e.g. asthma, rheumatoid arthritis, psoriasis, contact dermatitis, and atopic dermatitis. Furthermore the compounds of PCT/DK98/00008 was tested in vivo for anti-Inflammatory properties in the 12-O-tetradecanoylphorbol-13-acetate (TPA) induced murine chronic skin Inflammation model, (De Young, L. M. et al, Agents Actions, 26, 335–341 (1989); Carlson, R. P. et al., Agents Actions, 17, 197–204 (1985); Alford, J. G. et al, Agents Action, 37, (1992); Stanley, P. L. et al, Skin Pharmacol, 4, 262–271 (1991)). In this chronic skin Inflammation model the compounds had the same potency compared to the reference compound hydrocortisone.

The purpose of the present invention is to provide further pharmacologically active aminobenzophenone derivatives and related compounds.

This purpose is achieved with the novel aminobenzophenone derivatives according to the general formula I that are potent inhibitors of interleukin 1β (IL-1β) and tumour necrosis factor α (TNF-α) secretion in vitro, making them potentially useful for treatment of inflammatory diseases, in which the secretion and regulation of cytokines or more specifically interleukin 1β (IL-1β) and tumour necrosis factor α (TNF-α) are involved in the patho-genesis. The inhibition or down regulation of the cytokines is possibly due to an inhibition of MAP kinases.

SUMMARY OF THE INVENTION

The compounds of the present invention are represented by the general formula I below

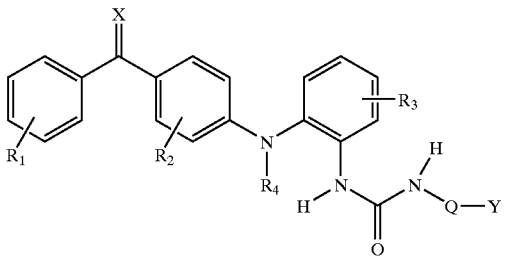

wherein $R_1$ and $R_2$ independently represent one or more, same or different substituents selected from the group consisting of halogen, hydroxy, mercapto, trifluoromethyl, amino, $(c_1-C_3)$alkyl, $(C_2-C_3)$olefinic group, $(C_1-C_3)$alkoxy, $(C_1-C_3)$alkylthio, $(C_1-C_6)$alkylamino, $(C_1-C_3)$alkoxycarbonyl, cyano, carbamoyl, phenyl, and nitro; $R_2$ further being represented by hydrogen;

$R_3$ represents hydrogen, halogen, hydroxy, mercapto, trifluoromethyl, amino, $(C_1-C_3)$alkyl, $(C_2-C_3)$olefinic group, $(C_1-C_3)$alkoxy, $(C_1-C_3)$alkylthio, $(C_1-C_6)$alkylamino, $(C_1-C_3)$alkoxycarbonyl, phenyl, cyano, carboxy, or carbamoyl;

$R_4$ represents hydrogen, $(C_1-C_3)$alkyl, or allyl;

Q represents a bond, —$SO_2$—, or —$C(R_6)(R_7)$(—O—C=O)—, in which formula $R_6$ and $R_7$ independently represent hydrogen, trifluoromethyl, or $(C_1-C_4)$alkyl;

Y represents $(C_1-C_{15})$alkyl, $(C_2-C_{15})$olefinic group, $(C_3-C_{10})$carbocyclic group, or phenyl, any of which is optionally substituted by one or more, same or different substituents represented by the formula $R_5$; or Y represents a group of formula —$(Z-O)_n$—Z, where Z is a $(C_1-C_3)$alkyl and n is an integer >1, and no continuous linear sequence of atoms in the group Y exceeds 15;

$R_5$ represents halogen, hydroxy, mercapto, trifluoromethyl, $(C_1-C_4)$alkyl, amino, $(C_1-C_3)$alkoxy, $(C_1-C_3)$alkylthio, $(C_1-C_6)$alkylamino, $(C_1-C_3)$alkoxycarbonyl, cyano, azido, nitro, —COOH, —$CONH_2$, —CONHR', or —CONRR' wherein R and R' stands for $(C_1-C_3)$alkyl;

X represents oxygen or sulphur, or a pharmaceutically acceptable salt thereof, or a hydrate or solvate thereof.

DETAILED DESCRIPTION OF THE INVENTION

Preferred Embodiments of the Invention

In compounds of the invention it is preferred that $R_1$ represents one or more, same or different substituents selected from the group consisting of fluoro, chloro, bromo, hydroxy, trifluoromethyl, amino, $(C_1-C_2)$alkyl, $(C_2-C_3)$alkenyl, $(C_1-C_3)$alkoxy, $(C_1-C_3)$alkoxycarbonyl, or cyano; $R_2$ represents one or more, same or different substituents selected from the group consisting of hydrogen, fluoro, chloro, bromo, hydroxy, trifluoromethyl, amino, $(C_1-C_2)$alkyl, $(C_2-C_3)$alkenyl, $(C_1-C_3)$alkoxy; $R_3$ represents one or more, same or different substituents selected: from the group consisting of hydrogen, fluoro, chloro, bromo, hydroxy, trifluoromethyl, $(C_1-C_3)$alkyl, $(C_2-C_3)$alkenyl, $(C_1-C_3)$alkoxy, $(C_1-C_3)$alkoxycarbonyl, cyano, or carboxy; $R_4$ represents hydrogen, $(C_1-C_2)$alkyl, or allyl; X represents oxygen; Q represents a bond, or —$SO_2$—; Y represents $(C_1-C_6)$alkyl; $(C_2-C_6)$alkenyl; $(C_3-C_6)$cycloalkyl; $(C_5-C_8)$ cycloalkene group; or phenyl; any of which is optionally substituted by one or more, same or different substituents selected from the group consisting of the formula $R_5$ as defined below, and $R_5$ represents fluoro, chloro, bromo, hydroxy, amino, $(C_1–C_2)$alkoxy, $(C_1–C_4)$alkylamino, $(C_1–C_3)$alkoxycarbonyl, cyano, azido, —COOH, —CONH$_2$, —CONHR', or —CONR'R' wherein R' represents $(C_1–C_2)$alkyl.

More preferred are compounds of formula I wherein $R_1$ represents one or more, same or different substituents selected from the group consisting of fluoro, chloro, bromo, hydroxy, methyl, or methoxy; preferably $R_1$ is methyl and most preferrably 2-methyl; $R_2$ represents one or more, same or different substituents selected from the group consisting of hydrogen, fluoro, chloro, bromo, hydroxy, methyl, or methoxy; preferably $R_2$ is Cl and most preferably 2-Cl; preferably $R_3$ represents hydrogen, methyl, methoxy, fluoro, chloro, or bromo; $R_4$ represents hydrogen; Y represents $(C_1–C_6)$alkyl, $(C_3–C_7)$cycloalkyl, or phenyl; any of which may be optionally substituted by one or more, same or different substituents selected from the group consisting of fluoro, chloro, bromo, hydroxy, amino, azido, $(C_1–C_3)$alkyl, $(C_1–C_2)$alkoxycarbonyl, cyano, —COOH, —CONH$_2$, and CON(CH$_3$)$_2$. Most preferably Y represents methyl, ethyl, n-propyl, isopropyl, n-butyl, t-butyl, cyclohexyl, hexyl, 6-chloro-hexyl, —(CH$_2$)$_2$COOCH$_2$CH$_3$, (CH$_2$)$_2$COOH, tolyl, or phenyl.

Further preferred compounds of general formula I are compounds wherein $R_1$, $R_2$, and $R_3$ represent one substituent. $R_1$ and $R_2$ preferably being in the ortho position.

Specific Compounds of the Invention Includes

1-Cyclohexyl-3-[2-[3-chloro-4-(2-methylbenzoyl)-phenylamino]phenyl]urea (Compound 101),
1-Ethyl-3-[2-[3-chloro-4-(2-methylbenzoyl)-phenylamino]phenyl]urea (Compound 102),
1-[2-[3-Chloro-4-(2-methylbenzoyl)-phenylamino]phenyl]-3-phenylurea (Compound 103),
1-Butyl-3-[2-[3-chloro-4-(2-methylbenzoyl)-phenylamino]phenyl]urea (Compound 104),
1-[2-[3-Chloro-4-(2-methylbenzoyl)-phenylamino]phenyl]-3-(4-methylphenylsulfonyl)urea (Compound 105),
1-[2-[3-Chloro-4-(2-methylbenzoyl)-phenylamino]phenyl]-3-(phenylsulfonyl)urea (Compound 106),
1-tert-Butyl-3-[2-[3-chloro-4-(2-methylbenzoyl)-phenylamino]phenyl]urea (Compound 107),
1-[2-[3-Chloro-4-(2-methylbenzoyl)-phenylamino]phenyl]-3-iso-propylurea (Compound 108),
1-[2-[3-Chloro-4-(2-methylbenzoyl)-phenylamino]phenyl]-3-propylurea (Compound 109),
1-Methyl-3-[2-[3-chloro-4-(2-methylbenzoyl)-phenylamino]phenyl]urea (Compound 110),
Ethyl 3-[2-[3-chloro-4-(2-methylbenzoyl)-phenylamino]phenyl3ureido)propionate (Compound 111),
1-Ethyl-3-[5-bromo-2-[3-chloro-4-(2-methylbenzoyl)-phenylamino]phenyl]urea (Compound 112),
3-[2-[3-Chloro-4-(2-methylbenzoyl)-phenylamino]phenyl] ureido)propionic acid (Compound 113),
1-Ethyl-3-[2-[3-chloro-4-(2-methylbenzoyl)-phenylamino]-5-fluoro-phenyl]urea (Compound 114),
1-Ethyl-3-[2-[3-chloro-4-(2-methylbenzoyl)-N-methyl-phenylamino]-5-fluoro-phenyl]urea (Compound 115),
1-Ethyl-3-[5-bromo-2-[3-chloro-4-(4-n-butyl-2-methylbenzoyl)-phenylamino]phenyl]urea (Compound 116),
1-Ethyl-3-[5-bromo-2-[3-chloro-4-(2,5-dimethylbenzoyl)-phenylamino]phenyl]urea (Compound 117),
1-Ethyl-3-[5-bromo-2-[3-chloro-4-(3-chloro-2-methylbenzoyl )-phenylamino]phenyl]urea (Compound 118),
1-Ethyl-3-[5-bromo-2-[3-chloro-4-(4-ethoxy-2-methylbenzoyl)-phenylamino]phenyl]urea (Compound 119),
1-Ethyl-3-[5-bromo-2-[3-ethoxy-4-(2-methylbenzoyl)-phenylamino]phenyl]urea (Compound 120),
1-Ethyl-3-[5-bromo-2-[3-chloro-4-(4-chloro-2-methylbenzoyl)-phenylamino]phenyl]urea (Compound 121),
1-Ethyl-3-[5-bromo-2-[3-chloro-4-(2,3-dimethylbenzoyl)-phenylamino]phenyl]urea (Compound 122),
1-Ethyl-3-[5-bromo-2-[3-fluoro-4-(4-methoxy-2-methylbenzoyl)-phenylamino]phenyl]urea (Compound 123),
1-Ethyl-3-[5-bromo-2-[3-chloro-4-(2,4,5-trimethylbenzoyl)-phenylamino]phenyl]urea (Compound 124),
1-Ethyl-3-[5-bromo-2-[3-chloro-4-(4-fluoro-2-methylbenzoyl)-phenylamino]phenyl]urea (Compound 125),
1-Ethyl-3-[5-bromo-2-[3-fluoro-4-(2-methylbenzoyl)-phenylamino]phenyl]urea (Compound 126),
and salts thereof with pharmaceutically acceptable acids, hydrates or solvates thereof.

As Used in the Specification, Unless Specified to the Contrary, the Following Terms have the Meaning Indicated "Alkyl" refers to any univalent group derived from an alkane by removal of a hydrogen atom from any carbon atom, and includes the subclasses of normal alkyl (n-alkyl), and primary, secondary and tertiary alkyl groups respectively, and having the number of carbon atoms specified, Including for example $(C_1–C_3)$alkyl, $(C_1–C_4)$alkyl, $(C_5)$alkyl, $(C_5–C_{15})$alkyl, $(C_6–C_{10})$alkyl, methyl, ethyl, n-propyl, isopropyl, n-butyl, isobutyl, sec-butyl, and t-butyl. Alkane refers to an acyclic branched or unbranched hydrocarbon having the general formula $C_nH_{2n+2}$, and therefore consisting entirely of hydrogen atoms and saturated carbon atoms.

"Olefinic group" refers to a straight or branched acyclic hydrocarbon having one or more carbon-carbon double bonds of either E or Z stereochemistry where applicable, and having the number of carbon atoms specified. The term includes, for example, $(C_2–C_{15})$olefinic group, preferably a $(C_2–C_{15})$alkenyl; $(C_2–C_3)$olefinic group, preferably a $(C_2–C_3)$alkenyl; vinyl; allyl; 1-butenyl; 2-butenyl; and 2-methyl-2-propenyl. Olefinic groups having only one carbon-carbon double bond, herein called alkenyl, are preferred.

"Alkoxy" refers broadly to a radical of the formula —OR, where R is alkyl as defined above, for example $(C_1–C_3)$ alkoxy, $(C_1–C_2)$alkoxy, methoxy, ethoxy, n-propoxy, and the like.

"$(C_1–C_3)$alkylthio" refers broadly to a radical of the formula —SR, where R is alkyl as defined above and includes methylthio, ethylthio, n-propylthio, and 2-propylthio.

"$(C_1–C_6)$alkylamino" refers broadly to a radical of the formula —NHR or —NR$_2$, where R is alkyl as defined above having from 1–6 carbon atoms and includes, for example, methylamino, dimethylamino, di-(n-propyl) amino, and n-butyl(ethyl)amino.

"$(C_1–C_3)$alkoxycarbonyl" refers broadly to a radical of the formula —COOR, where R is alkyl as defined above and includes methoxycarbonyl, ethoxycarbonyl, n-propoxycarbonyl, and i-propoxycarbonyl.

"$(C_3–C_{10})$monocyclic hydrocarbon group" includes the saturated cycloalkanes and unsaturated cyclic olefins, such as cycloalkenes having one endocyclic double bond, and having from 3–10 carbon atoms, and includes, for example, ($C_3$–$C_8$)cycloalkyl, cyclopropyl, cyclopentyl, cyclohexyl, and cyclooctyl, ($C_3$–$C_{10}$)cycloalkene group, and ($C_3$–$C_8$) cycloalkene group. Specific examples are cycloprop-2-enyl, cyclobut-2-enyl, cyclopent-2-enyl, cyclohex-3-enyl, and cyclonon-4-enyl.

"Amino" means the group —$NH_2$.

"Carbamoyl" refers to any one of the groups —$CONH_2$, —CONHR, and —CONRR' where R and R' represent alkyl as defined above.

"Carboxy" refers to a radical of the formula —COOH.

"Halogen" means the same or different of fluoro, chloro, bromo, and iodo; fluoro, chloro, and bromo being preferred.

The phenyl group of $R_1$ and $R_2$ may optionally be substituted, e.g. with hydroxy; amino; nitro; cyano; halogen, preferably fluoro, chloro, or bromo; methyl; or methoxy.

The compounds can be used in the form of their salts which are formed with pharmaceutically acceptable inorganic or organic acids, such as hydrochloric, hydrobromic and hydroiodic acid, phosphoric acid, sulphuric acid, nitric acid, p-toluenesulphonic acid, methane-sulphonic acid, formic acid, acetic acid propionic acid, citric acid, tartaric acid, succinic acid, benzoic acid, maleic acid, these examples being considered as non-limiting for the invention.

Pharmacological Methods

To study the effect of the compound of the present invention in vitro the inhibition of the IL-1β and TNF-α secretion was measured using the following procedure:

Cytokine production was measured in the media from lipopolysaccharide (LPS) stimulated peripheral blood mononuclear cells. The mononuclear cells were isolated from human. peripheral blood by Lymphoprep® (Nycomed, Norway) fractionation and suspended in RPMI 1640 (growth medium) with foetal calv serum (FCS, 2%), at a concentration of $5 \times 10^5$ cells/ml. The cells were incubated in 24-well tissue culture plates in 1 ml aliquots. Test compounds were dissolved in dimethylsulfoxide (DMSO, 10 mM) and were diluted with the medium. Compounds were added to the cells for 30 minutes, then LPS (1 mg/ml final concentration) was added. The plates were incubated for 18 hours, and the concentration of IL-1β and TNF-α in the medium was determined by enzyme-linked immunosorbent assays. The median inhibitory concentrations ($IC_{50}$) of the compounds were calculated. The results are shown in Table 1 below.

The compounds of the present invention also show similar activities in the ability to inhibit PMN (polymorphonuclear) superoxide secretion which is also indicative of potentially useful anti-inflammatory drugs The compounds were tested using the following procedure:

Human polymorphonuclear (PMN) granulocytes were Isolated from human blood by dextran sedimentation, Lymphoprep® fractionation and hypotonic lysis of contaminating erythrocytes.

Superoxide anion generation was measured as the superoxide dismutase inhibitable reduction of ferricytochrome C (Madhu, S. B. et al, Inflammation, 16 241, (1992)). The cells were suspended in Hanks' balanced salt solution, and incubated for 10 minutes at 37° C. with test compounds. The cells were primed by the addition of TNF-α (3 ng/ml final concentration) for 10 minutes, and then ferricytochrome C, (final concentration 750 μg/ml), bovine serum albumin (BSA, final concentration 1 mg/ml) and formyl-methionyl-leucyl-phenylalanine (fMLP, final concentration $10^{-7}$ M) were added for 3 minutes. The cells were chilled on ice, and were spun down. The optical densities in the cell-free supernatant was measured in a spectrophotometer. The median Inhibitory concentration ($IC_{50}$) of the compounds was calculated. The results are shown in Table 1.

TABLE 1

Inhibition of cytokines and PMN-superoxide production in vitro by compounds of the present invention.

| Comp No.; Ex. No. | The median inhibition concentration ($IC_{50}$, nM) of | | |
|---|---|---|---|
| | IL-1β | TNF-α | PMN-superoxide |
| 101, Ex. 1 | 13 | 5.0 | 4.0 |
| 102, Ex. 2 | 22 | 2.2 | 13 |
| 114, Ex. 14 | 7.9 | 3.2 | 4.0 |
| ref. a) | 13 | 7.1 | 5.0 |
| ref. b) | >1000 | 631 | 316 | ref. a) 4-(2-Aminophenylamino)-2-chloro-2'-methylbenzophenone, compound 106 disclosed in PCT/DK98/00008.
ref. b) 1-Ethyl-3-[2-(4-benzoyl-phenylamino)phenyl]urea of the general formula I in PCT/DK98/00008.

These results show that the compounds of the present Invention are able to inhibit the production of IL-1β, TNF-α and PMN-superoxide showing pharmacological activities comparable to compounds of the prior art, thus making them potentially useful In the treatment of inflammatory diseases.

To study the compounds of the present invention in vivo the 12-O-tetradecanoylphorbol-13-acetate (TPA) induced murine chronic skin inflammation model can be used (De Young, L. M. et al, Agents Actions, 26, 335–341 (1989); Carlson, R. P. et al, Agents Actions, 17, 197–204 (1985); Alford, J. G. et al, Agents Action, 37, (1992); Stanley, P. L. et al, Skin Pharmacol, 4, 262–271 (1991)), cf. description of method in PCT/DK98/00008 hereby incorporated by reference. These results shows that the compounds of the present invention are of the same potency compared to known reference compounds, e.g. hydrocortisone with its known side effects, whereas the compounds of the present invention are well tolerated and are non-toxic. Some members of the present class of compounds show a very low absorption, thus making them especially useful in the treatment of various dermatological diseases. In general, they may be administered by e.g. oral, intravenous, intranasal, topically or transdermal routes.

Method of Preparation

The compounds of the present invention can be prepared in a number of ways well known to those skilled in the art of organic synthesis. The compounds of the present invention can be synthesised using the methods outlined below, together with methods known in the art of synthetic organic chemistry, or variations thereof as appreciated by those skilled in the art. Preferred methods include, but are not limited to, those described below. The novel compounds of formula I may be prepared using the reactions and techniques described in this section. The reactions are performed in solvents appropriate to the reagents and materials employed and are suitable for the transformations being effected. Also, in the synthetic methods described below, It is to be understood that all proposed reaction conditions, including choice of solvent, reaction atmosphere, reaction temperature, duration of experiment and work-up procedures, are chosen to be conditions of standard for that reaction, which should be readily recognised by one skilled in the art. It is understood by one skilled in the art of organic synthesis that the functionality present on various portions of the educt molecule must be compatible with the reagents and reactions proposed. Not all compounds of formula I falling into a given class may be compatible with some of the reaction conditions required in some of the methods described. Such restrictions to the substituents which are compatible with the reaction conditions will be readily apparent to one skilled in the art and alternate methods can be used.

Compounds according to the present Invention may be prepared by a process comprising coupling of an amine of the formula II with an isocyanates of the formula III or a suitable activated derivative with the formula IV; e.g. carbamic acid chlorides and carbamic acid esters (phenoxy, 4-nitrophenoxy and 2,4,5-trichlorophenoxy) or other suitable activated derivatives of the formula IV, as shown in scheme 1, where $R_1$, $R_2$, $R_3$, $R_4$, Q, X, and Y are as defined in general formula I, except that any substituents or functional group which are potentially reactive in the coupling reaction may themselves be protected before the coupling reaction is performed and subsequently removed.

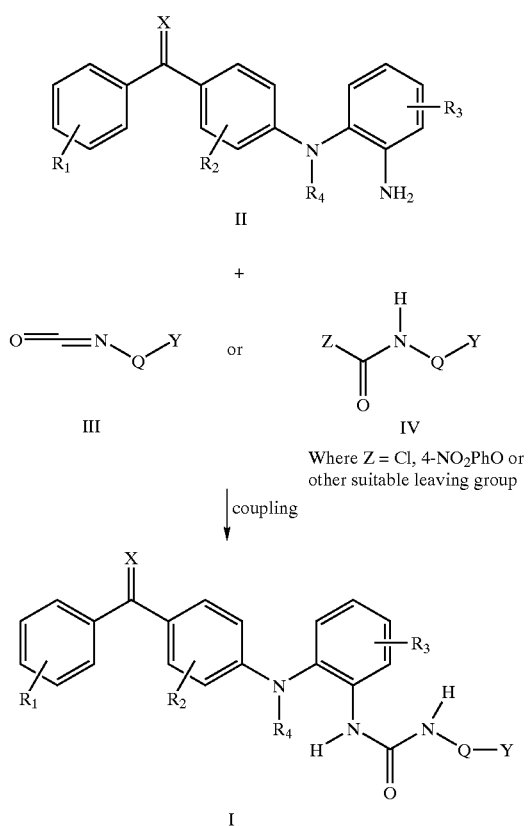

and $R_1$, $R_2$, $R_3$, $R_4$, X, Q, and Y have the above meanings.
Scheme 1

Compounds accordingly to the present invention with the general formula II(X=O) may be prepared by several methods known to those skilled in the art of organic synthesis. One useful sequence is shown in scheme 2 were the key process comprising coupling of an amine of the formula VII with an fluoride, chloride, bromide, iodide, or triflate with the formula VIII, as shown in Scheme 2, where $R_1$, $R_2$, $R_3$, and, $R_4$ are as defined in general formula I, to give a coupled product with the general formula VI, except that any substituents or functional group which are potentially reactive in the coupling reaction may themselves be protected before the coupling reaction Is performed and subsequently removed. This compound VI may then be reduced to the corresponding amine with the general formula II by treatment with standard reducing agents. Examples of such reducing agents include, but are not limited to, stannous chloride dihydrate; hydrogen, ammonium formiate, or hydrazine hydrate and a catalytic amount of palladium on carbon.

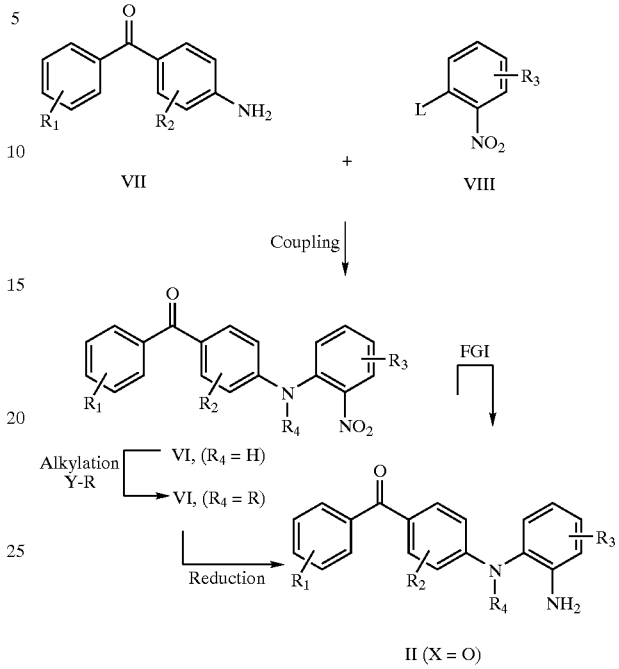

L: Br, I, OSO$_2$CF$_3$, or F and Cl
Y: Cl, Br, I, OSO$_2$CF$_3$, OSO$_2$CH$_3$, or OTs
FGI: Functional group interconversion and $R_1$, $R_2$, $R_3$, and $R_4$ have the above meanings.
Scheme 2

The coupling reaction is carried out using any of the methods for the formation of diphenylamines known to one skilled in the art of organic synthesis. The preferred method is the nucleophilc aromatic substitution method which comprising coupling of an amine with an arylfluoride or arylchloride in the presence of a base, in an suitable solvent. Especially potassium-tert-butoxide (KOt-Bu), sodium-tert-butoxide (NaOt-Bu), sodium hydrid (NaH), and potassium hydride (KH) have proven to be the best bases in this process, but other bases may be used as well.

The reaction is typically performed at ambient temperature (20–25° C.) in dipolar aprotic solvents like dimethylsulfoxide (DMSO), dimethylformamide (DMF), or N-methylpyrrolidone (NMP) under an inert atmosphere like argon or nitrogen.

Alternatively, the coupling reaction can be done by the palladium catalysed amination method which comprising coupling of an amine with an arylhalogenide (iodide, bromide, triflate, or in some cases chloride) In the presence of a base, a suitable Pd source, and a suitable phosphine ligand in an inert solvent.

The palladium compound used in the process is not particularly limited, and as specific examples are
palladium(II) acetate, palladium(II) chloride, palladium (II) bromide, dichlorobis(triphenyl-phosphine) palladium(II), tetrakis(triphenylphosphine)palladium (0), tris(dibenzylidene-acetone)dipalladlium(0). The preferred ligand include, but are not limited to, racemic or non-racemic 2,2'-bis(diphenylphosphino)-1,1'-binaphthyl (hereinafter referred to as BINAP), tri-o-tolylphosphine, tri-tert-butylphosphine, 1,1'-bis (diphenylphosphino)-ferrocene, bis[(2-diphenylphosphino)phenyl]ether (DPEphos), 2-dicyclohexylphosphanyl-2'-dimethylaminobiphenyl, 2-(di-tert-butylphosphino)biphenyl, and 9,9-dimethyl-4,6-bis(diphenylphosphino)xanthene (Xantphos). The amount of palladium and ligand used in this process Is typically in the range 0.1 to 10% by mole relative to the amount of the aromatic halide (or triflate) used. Especially sodium-tert-butoxide (NaOt-Bu) and caesium carbonate ($Cs_2CO_3$) have proven to be the best bases in this process, but other bases may be used as well. The reaction is typically performed at elevated temperature (80–120° C.) in inert solvents like 1,4-dioxane, toluene, benzene and tetrahydrofurane under an inert atmosphere like argon or nitrogen.

Compounds according to the present invention in which $R_4$ is not hydrogen may be prepared by a process comprising coupling of an amine of the formula VI ($R_4$=H) with an alkylating agent, as shown in scheme 2, where $R_1$, $R_2$, $R_3$, and, $R_4$ are as defined in general formula I, except that any substituents or functional group which are potentially reactive in the coupling reaction may themselves be protected before the coupling reaction is performed and subsequently removed.

Typically alkylating agents of the general formula R-Y include, but are not limited to, iodides (Y=I), bromides (Y=Br), chlorides (Y=Cl) and sulfonates (Y=$OSO_2R'$, where R' represents methyl, trifluoromethyl or 4-methylphenyl).

Compounds according to the present invention may in special cases be prepared by a simple functional group interconversion (FGI), meaning a standard process, known to those skilled in the art of organic synthesis, where a functional group in compounds with the general formula I (or any other intermediate described herein) is transformed into a different functional group in one or more synthetic steps, leading to a new compound with the general formula I. Examples of such processes are, but are not limited to, hydrolysis of an ester to give an acid under basic conditions; deprotection of an methylether to give an phenol by treatment with e.g. borontribromide ($BBr_3$); and catalytic hydrogenation of an olefin to give an saturated hydrocarbon.

Compounds according to the present invention in which C=X represents—(CS)—may be prepared from compounds of the invention (or any other intermediate described herein) in which C=X represents —(CO)— by a process using an appropiate thiocarbonylating agent such as phosphorous pentasulfide ($P_4S_{10}$), or Lawesson's reagent (2,4-bis(4-methoxyphenyl)-1,3,2,4-dithiaphosphetane-2,4-disulfide) or the like.

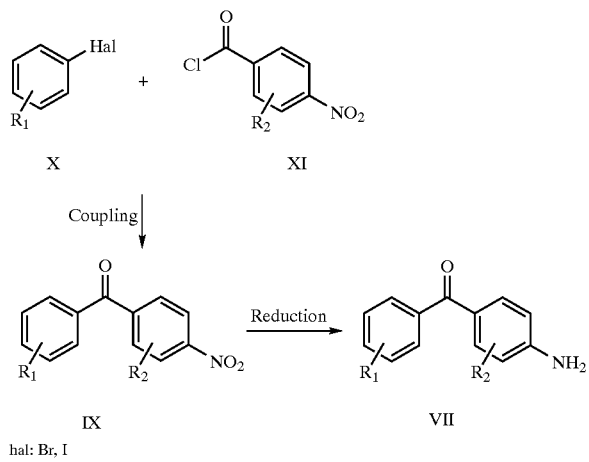

hal: Br, I and $R_1$, and $R_2$ have the above meanings.
SCHEME 3

Compounds accordingly to the present invention with the general formula VII may be prepared by several methods known to those skilled in the art of organic synthesis. One useful sequence is shown in Scheme 3. The key step comprises coupling of a bromide (or Iodide) with the general formula X with an acid chloride with the general formula XI to afford the benzophenone with the general formula IX. This compound IX may then be reduced to the corresponding amine with the general formula VII by treatment with standard reducing agents. Examples of such reducing agents include, but are not limited to, stannous chloride dihydrate; hydrogen, ammonium formiate, or hydrazine hydrate and a catalytic amount of palladium on carbon. The coupling reaction is done by transforming the bromide (X) into a reactive organometallic intermediate, e.g. by treatment with butyllithium to afford the lithium derivative or by treatment with magnesium to afford the magnesium derivative. The reactivity of this intermediate is then modulated by transmetallation to e.g. zinc, by treatment with $ZnCl_2$, $ZnBr_2$, or $ZnI_2$. This organozinc compound is then coupled with the acid chloride, with the general formula XI, under the influence of a palladium(O) complex in catalytic amount. Examples of such catalyst include but are not particularly limited to tetrakis(triphenylphosphine)palladium(O), tetrakis(triphenylarsine)-palladium(O), dichlorobis (triphenylphosphine)palladium(II), or benzylchlorobis (triphenyl-phosphine)palladium(II).

It may be more advantageous in some cases to alter the sequence of the processes described above. The described sequence of processes is not considered as being limited for the preparation of the compounds of the present invention with the general formula I and alteration of the reaction sequence is an obvious alternative for those skilled in the art of organic synthesis.

The present compounds are intended for use in pharmaceutical compositions which are useful in the treatment of the above mentioned diseases.

The amount required of a compound of formula I (hereinafter referred to as the active ingredient) for therapeutic effect will, of course, vary both with the particular compound, the route of administration and the mammal under treatment. A suitable dose of a compound of formula I for systemic treatment is 0.1 to 200 mg/kg bodyweight, the most preferred dosage being 0.2 to 50 mg/kg of mammal bodyweight, administered one or more times daily.

While it is possible for an active ingredient to be administered alone as the raw chemical, it is preferable to present it as a pharmaceutical formulation. Conveniently, the active Ingredient comprises from 0.1% to 100% by weight of the formulation.

Conveniently, dosage units of a formulation contain between 0.07 mg and 1 g of the active ingredient. For topical administration, the active ingredient preferably comprises from 1% to 20% by weight of the formulation but the active ingredient may comprise as much as 50% w/w. Formulations suitable for nasal or buccal administration may comprise 0.1% to 20% w/w. for example about 2% w/w of active ingredient.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for veterinary and human medical use, of the present invention comprise an active ingredient in association with a pharmaceutically acceptable carrier therefore and optionally other therapeutic ingredient(s). The carrier(s) must be "acceptable" in the sense of being compatible with the other ingredients of the formulations and not deleterious to the recipient thereof.

The formulations include those in a form suitable for oral, ophthalmic, rectal, parenteral (including subcutaneous, intramuscular and intravenous), transdermal, intra-articular, topical, nasal, or buccal administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier such as cocoa butter, or in the form of an enema. Formulations suitable for parenteral administration conveniently comprise a sterile oily or aqueous preparation of the active ingredient which is preferably Isotonic with the blood of the recipient.

Formulations suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops.

Formulations suitable for administration to the nose or buccal cavity include powder, self-propelling and spray formulations, such as aerosols and atomizers. In addition the aforementioned ingredients, the formulations of this invention may include one or more additional ingredients.

The compositions may further contain other therapeutically active compounds usually applied in the treatment of the above mentioned pathological conditions, for instance glucocorticoids, vitamin D's, anti-histamines, platelet activating factor (PAF) antagonists, anticolinergic agents, methyl xanthines, β-adrenergic agents, salicylates, indomethacin, flufenamate, naproxen, timegadine, gold salts, penicillamine, serum cholesterol-reducing agents, retinoids, zinc salts, and salicylazosulfapyridin (Salazopyrin).

The novel compounds of the invention are of value in the human and veterinary practice as systemic and topical therapeutic agents for the treatment and prevention of diseases. The novel compounds show anti-acne properties and, i.a., anti-inflammatory and cytokine regulating effects possibly due to MAP kinase inhibition, and are useful in the treatment and prophylaxis of asthma, allergy, arthritis, including rheumatoid arthritis and spondylo-arthritis, gout, atherosclerosis, chronic inflammatory bowel disease (Crohn's disease), proliferative and inflammatory skin disorders, such as psoriasis, atopic dermatitis, uveitis, septic shock, AIDS, and osteoporosis.

The invention will now be further described in the following general procedures, preparations and examples:

EXAMPLES

General Procedures, Preparations and Examples

The exemplified compounds I are listed in table 2. All melting points are uncorrected. For $^1$H and $^{13}$C nuclear magnetic resonance (NMR) spectra (300 MHz) chemical shift values (δ) (in ppm) are quoted, unless otherwise specified, for deuteriochloroform and hexadeuterodimethylsulfoxide solutions relative to internal tetramethylsilane (δ 0.00) or chloroform ($^1$H NMR δ 7.25, $^{13}$C NMR δ 76.81). The value for a multiplet (m), either defined (doublet (d), triplet (t), quartet (q)) or not at the approximate mid point is given unless a range is quoted (s singlet, b broad). The organic solvents used were anhydrous. The term "chromatography" refers to column chromatography using the flash technique and was performed on silica gel.

The following abbreviations have been used throughout:

| | |
|---|---|
| AgOAc | Silver acetate |
| BTC | Bis(trichloromethyl) carbonate |
| CDCl$_3$ | Deuteriochloroform |
| DMF | N,N-Dimethylformamide |
| DMSO-d$_6$ | Hexadeuterodimethylsulfoxide |
| Et$_3$N | Triethylamine |
| EtOAc | Ethyl acetate |
| Et$_2$O | Diethylether |
| HMPA | Hexamethylphosphorous triamide |
| NMM | N-Methylmorpholine |
| THF | Tetrahydrofurane |
| TLC | Thin layer chromatography |

TABLE 2

Compounds of general formula I

| Comp. No. | Example No | X | R$_1$ | R$_2$ | R$_3$ | R$_4$ | Q | Y |
|---|---|---|---|---|---|---|---|---|
| 101 | 1 | O | 2-Me | 2-Cl | H | H | Bond | -cyclohexyl |
| 102 | 2 | O | 2-Me | 2-Cl | H | H | Bond | —CH$_2$CH$_3$ |
| 103 | 3 | O | 2-Me | 2-Cl | H | H | Bond | -phenyl |
| 104 | 4 | O | 2-Me | 2-Cl | H | H | Bond | —(CH$_2$)$_3$CH$_3$ |
| 105 | 5 | O | 2-Me | 2-Cl | H | H | —(SO$_2$)— | -tolyl |
| 106 | 6 | O | 2-Me | 2-Cl | H | H | —(SO$_2$)— | -phenyl |
| 107 | 7 | O | 2-Me | 2-Cl | H | H | Bond | —C(CH$_3$)$_3$ |
| 108 | 8 | O | 2-Me | 2-Cl | H | H | Bond | —CH(CH$_3$)$_2$ |
| 109 | 9 | O | 2-Me | 2-Cl | H | H | Bond | —(CH$_2$)$_2$CH$_3$ |
| 110 | 10 | O | 2-Me | 2-Cl | H | H | Bond | —CH$_3$ |

TABLE 2-continued

Compounds of general formula I

| Comp. No. | Example No | X | $R_1$ | $R_2$ | $R_3$ | $R_4$ | Q | Y |
|---|---|---|---|---|---|---|---|---|
| 111 | 11 | O | 2-Me | 2-Cl | H | H | Bond | —$(CH_2)_2COOCH_2CH_3$ |
| 112 | 12 | O | 2-Me | 2-Cl | 4-Br | H | Bond | —$CH_2CH_3$ |
| 113 | 13 | O | 2-Me | 2-Cl | H | H | Bond | —$(CH_2)_2COOH$ |
| 114 | 14 | O | 2-Me | 2-Cl | 4-F | H | Bond | —$CH_2CH_3$ |
| 115 | 15 | O | 2-Me | 2-Cl | 4-F | $CH_3$ | Bond | —$CH_2CH_3$ |
| 116 | 16 | O | 2-Me, 4-Bu | 2-Cl | 4-Br | H | Bond | —$CH_2CH_3$ |
| 117 | 17 | O | 2-Me, 5-Me | 2-Cl | 4-Br | H | Bond | —$CH_2CH_3$ |
| 118 | 18 | O | 2-Me, 3-Cl | 2-Cl | 4-Br | H | Bond | —$CH_2CH_3$ |
| 119 | 19 | O | 2-Me, 4-OEt | 2-Cl | 4-Br | H | Bond | —$CH_2CH_3$ |
| 120 | 20 | O | 2-Me | 2-OEt | 4-Br | H | Bond | —$CH_2CH_3$ |
| 121 | 21 | O | 2-Me, 4-Cl | 2-Cl | 4-Br | H | Bond | —$CH_2CH_3$ |
| 122 | 22 | O | 2-Me, 3-Me | 2-Cl | 4-Br | H | Bond | —$CH_2CH_3$ |
| 123 | 23 | O | 2-Me, 4-OMe | 2-F | 4-Br | H | Bond | —$CH_2CH_3$ |
| 124 | 24 | O | 2-Me, 4-Me, 5-Me | 2-Cl | 4-Br | H | Bond | —$CH_2CH_3$ |
| 125 | 25 | O | 2-Me, 4-F | 2-Cl | 4-Br | H | Bond | —$CH_2CH_3$ |
| 126 | 26 | O | 2-Me | 2-F | 4-Br | H | Bond | —$CH_2CH_3$ |

The numbering in Table 2 refers to the numbering in the formula below

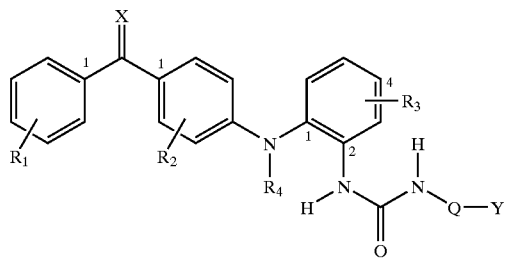

General procedure 1: Coupling of compounds of the general formula II with compounds of the general formula III to give compounds of the general formula I, or a protected derivative thereof.

To a solution or suspension of an amine (1.0 mmol), with the general formula II, in an inert solvent (10 ml, typically toluene, pyridine or EtOAc) was slowly added an isocyanate (1.1–2.5 mmol), with the general formula III. Stirring was continued at room temperature for 24 h or until the starting material had disappeared as seen on TLC. The reaction mixture was concentrated in vacuo to afford the crude product. The crude product was typically either purified by chromatography and/or crystallized to give the title compound.

Example 1

1-Cyclohexyl-3-[2-[3-chloro-4-(2-methylbenzoyl)-phenylamino]phenyl]urea (Compound 101)

General procedure: 1

Starting compound II: 4-(2-Aminophenylamino)-2-chloro-2'-methylbenzophenone

Starting compound III: Cyclohexyl isocyanate

Solvent for the reaction: EtOAc

Purification: Chromatography using EtOAc/hexane 1:1 as eluant followed by trituration from $Et_2O$ Mp: 154–155° C.

$^1$H NMR (DMSO-$d_6$): δ 8.34 (s,1H), 8.05 (d,1H), 7.76 (s,1H), 7.41 (m,1H), 7.35–7.10 (m,6H), 6.95 (m,1H), 6.68 (m;2H), 6.57 (m,1H), 3.44 (m,1H), 2.29 (s,3H), 1.77 (m,2H), 1.63 (m,2H), 1.52 (m,1H), 1.40–1.00 (m,5H)

Example 2

1-Ethyl-3-[2-[3-chloro-4-(2-methylbenzoyl)-phenylamino]phenyl]urea (Compound 102)

General procedure: 1

Starting compound II: 4-(2-Aminophenylamino)-2-chloro-2'-methylbenzophenone

Starting compound III: Ethyl isocyanate

Solvent for the reaction: Pyridine

Purification: The title compound crystallized on the addition of water to the reaction mixture. Filtration, washing (water), and drying afforded a pure crystalline product.

Mp: 158.3–159.8° C.

$^1$H NMR (DMSO-$d_6$): δ 8.34 (s,1H), 8.04 (d,1H), 7.79 (s,1H), 7.42 (m,1H), 7.10–7.34 (m,6H), 6.96 (m,1H), 6.67 (m,2H), 6.57 (m,1H), 3.07 (m,2H), 2.29 (s,3H), 1.02

Example 3

1-[2-[3-Chloro-4-(2-methylbenzoyl)-phenylamino]phenyl]-3-phenylurea (Compound 103)

General procedure: 1, except the reaction mixture was heated to 100° C. for 4 h

Starting compound II: 4-(2-Aminophenylamino)-2-chloro-2'-methylbenzophenone

Starting compound III: Phenyl isocyanate

Solvent for the reaction: Pyridine

Purification: Crystallization from $Et_2O$

Mp: 163–166.8° C.

$^1$H NMR (DMSO-$d_6$): δ 9.15 (s,1H), 8.43 (s,1H), 8.13 (s,1H), 8.09 (d,1H), 7.10–7.50 (m,11H), 7.05 (m,1H), 6.96 (m,1H), 6.75 (d,1H), 6.63 (dd,1H), 2.28 (s,3H)

Example 4

1-Butyl-3-[2-[3-chloro-4-(2-methylbenzoyl)-phenylamino]phenyl]urea (Compound 104)

General procedure: 1, except the reaction mixture was heated to 100° C. for 4 h

Starting compound II: 4-(2-Aminophenylamino)-2-chloro-2'-methylbenzophenone

Starting compound III: Butyl isocyanate

Solvent for the reaction: Toluene

Purification: Chromatography using EtOAc/pentane 3:7 as eluant followed by crystallization from Et$_2$O Mp: 104–106° C.

$^1$H NMR (DMSO-d$_6$): δ 8.35 (s,:1H), 8.04 (d,1H), 7.80 (s,1H), 7.41 (m,1H), 7.08–7.34 (m,6H), 6.97 (m,1H), 6.70 (t,1H), 6.66 (d,1H), 6.57 (dd,1H), 3.05 (m,2H), 2.29 (s,3H), 1.20–1.40 (m,4H), 0.86 (t,3H)

Example 5

1-[2-[3-Chloro-4-(2-methylbenzoyl)-phenylamino]phenyl]-3-(4-methylphenylsulfonyl)urea (Compound 105)

General procedure: 1

Starting compound II: 4-(2-Aminophenylamino)-2-chloro-2'-methylbenzophenone

Starting compound III: p-Toluenesulfonyr isocyanate

Solvent for the reaction: Toluene

Purification: The product was filtered off and washed with Et$_2$O to afford the title compound.

Mp: 180–185° C.

$^{13}$C NMR (DMSO-d$_6$): δ 195.3, 150.3, 149.0, 143.9, 139.1, 136.7, 136.4, 133.9, 133.4, 133.4, 131.0, 130.7, 129.5, 129.3, 129.2, 128.8, 127.2, 126.4, 126.3, 125.6, 125.5, 124.1, 120.5, 114.7, 111.4, 20.9, 19.7

Example 6

1-[2-[3-Chloro-4-(2-methylbenzoyl)-phenylamino]phenyl]-3-(phenylsulfonyl)urea (Compound 106)

General procedure: 1

Starting compound II: 4-(2-Aminophenylamino)-2-chloro-2'-methylbenzophenone

Starting compound III: Benzenesulfonyl isocyanate

Solvent for the reaction: Toluene

Purification: The product was filtered off and washed with Et$_2$O to afford the title compound.

Mp: 196–201° C.

$^{13}$C NMR (DMSO-d$_6$): δ 195.3, 150.3, 139.6, 139.1, 136.4, 133.8, 133.7, 133.4, 131.7, 131.0, 130.7, 130.3, 129.3, 129.0, 128.8, 128.4, 127.2, 126.4, 126.4, 125.6, 125.5, 124.1, 120.5, 116.3, 114.7, 111.4, 19.7

Example 7

1-tert-Butyl-3-[2-[3-chloro-4-(2-methylbenzoyl)-phenylamino]phenyl]urea (Compound 107)

General procedure: 1, except the reaction mixture was heated to 50° C. for 6 h

Starting compound II: 4-(2-Aminophenylamino)-2-chloro-2'-methylbenzophenone

Starting compound III: tert-Butyl isocyanate

Solvent for the reaction: Pyridine

Purification: The title compound crystallized on the addition of water to the reaction mixture. Filtration, washing (water), and drying afforded a pure crystalline product.

Mp: 159–161° C. $^1$H NMR (DMSO-d$_6$): δ8.32 (s,1H), 8.05 (d,1H), 7.73 (s,1H), 7.07–7.46 (m,7H), 6.95 (m,1H), 6.67 (d,1H), 6.60 (s,1H), 6.57 (dd,1H), 2.29 (s,3H), 1.26 (s,9H)

Example 8

1-[2-[3-Chloro-4-(2-methylbenzoyl)-phenylamino]phenyl]-3-iso-propylurea (Compound 108)

General procedure: 1

Starting compound II: 4-(2-Aminophenylamino)-2-chloro-2'-methylbenzophenone

Starting compound III: iso-Propyl isocyanate

Solvent for the reaction: Toluene

Purification: Chromatography using EtOAc/pentane 3:7 as eluant followed by crystallization from water Mp: 103–106° C.

$^1$H NMR (DMSO-d$_6$): δ 8.34 (s,1H), 8.07 (d,1H), 7.74 (s,1H), 7.42 (m,1H), 7.10–7.35 (m,6H), 6.95 (m,1H), 6.66 (m,2H), 6.56 (dd,1H), 3.71 (m,1H), 2.29 (s,3H), 1.06.(d,6H)

Example 9

1-[2-[3-Chloro-4-(2-methylbenzoyl)-phenylamino]phenyl]-3-propylurea (Compound 109)

General procedure: 1

Starting compound II: 4-(2-Aminophenylamino)-2-chloro-2'-methylbenzophenone

Starting compound III: Propyl isocyanate

Solvent for the reaction: Pyridine

Purification: Crystallization from Et$_2$O

Mp: 133–135° C.

$^{13}$C NMR (DMSO-d$_6$): δ 195.2, 155.1, 150.7, 139.4, 136.3, 136.2, 133.5, 130.9, 130.5, 128.6, 128.3, 126.1, 125.8, 125.5, 121.8, 120.3, 114.7, 111.4, 40.8, 22.8, 19.6, 11.3

Example 10

1-Methyl-3-[2-[3-chloro-4-(2-methylbenzoyl)-phenylamino]phenyl]urea (Compound 110)

General procedure: 1

Starting compound II: 4-(2-Aminophenylamino)-2-chloro-2'-methylbenzophenone

Starting compound III: Methylisocyanate

Solvent for the reaction: Pyridine

Purification: Crystallization from Et$_2$O

Mp: 154–155° C.

$^1$H NMR (DMSO-d$_6$): δ 8.35 (s,1H), 8.01 (d,1H), 7.84 (s,1H), 7.40 (m,1H), 7.09–7.35 (m,6H), 6.97 (m,1H), 6.68 (d,1H), 6.59 (m,2H), 2.61 (d,3H), 2.29 (s,3H)

Example 11

Ethyl 3-[2-[3-chloro-4-(2-methylbenzoyl)-phenylamino]phenyl]ureido)propionate (Compound 111)

General procedure: 1

Starting compound II: 4-(2-Aminophenylamino)-2-chloro-2'-methylbenzophenone

Starting compound III: Ethyl 3-isocyanatopropionate

Solvent for the reaction: Pyridine

Purification: Chromatography using EtOAc/pentane 3:2 as eluant to give the title compound as a syrupy $^{13}$C NMR (CDCl$_3$): δ 196.7, 172.9, 156.3, 148.8, 139.2, 137.8, 135.0, 133.6, 133.0, 131.9, 131.3, 130.9, 129.6, 128.5, 125.4, 125.4, 124.2, 123.8, 116.4, 112.7, 60.9, 36.0, 34.7, 20.4, 14.1

Example 12

1-Ethyl-3-[5-bromo-2-[3-chloro-4-(2-methylbenzoyl)-phenylamino]phenyl]urea (Compound 112)

General procedure: 1

Starting compound II: 4-[(2-Amino-4-bromo-phenyl)amino]-2-chloro-2'-methylbenzophenone Starting compound III: Ethyl isocyanate Solvent for the reaction: Pyridine Purification: Crystallization from a mixture of EtOAc/pentane 1:1

Mp: 125–127° C.

$^{13}$C NMR (CDCl$_3$): δ 197.5, 155.8, 149.2, 138.9, 137.7, 135.2, 135.0, 133.6, 131.4, 131.2, 129.8, 129.7, 128.2, 126.8, 126.2, 125.5, 125.0, 118.7, 116.1, 112.3, 35.2, 20.5, 15.2

Example 13

3-[2-[3-Chloro-4-(2-methylbenzoyl)-phenylamino]phenyl]ureido)propionic acid (Compound 113)

Ethyl 3-[2-[3-chloro-4-(2-methylbenzoyl)-phenylamino]phenyl]ureido) propionate (Compound 111, 6.25 mmol) and K$_2$CO$_3$ (9.4 mmol) was stirred in a mixture of MeOH (25 ml) and water (8 ml) for 4 h at ambient temperature. More water (13 ml) was added and the reaction mixture was stirred overnight. The reaction mixture was poured into EtOAc and water. pH was adjusted to approximately 4 with glacial acetic acid. The organic phase was separated, washed with water and brine, then dried (MgSO$_4$), filtered and concentrated in vacuo to afford a weakly coloured oily crude product. Purification was done by chromatography using CH$_2$Cl$_2$/MeOH/CH$_3$COOH 250:10:1 as eluant to afford the title compound.

$^{13}$C NMR (CDCl$_3$): δ 197.5, 176.3, 157.0, 148.9, 138.9, 137.9, 134.9, 133.5, 132.8, 131.7, 131.3, 131.1, 129.8, 128.4,.125.6, 125.5, 124.4, 123.9, 116.3, 112.6, 35.8, 34.5, 20.7, 20.5

Example 14

1-Ethyl-3-[2-(3-chloro-4-(2-methylbenzoyl)-phenylamino]-5-fluoro-phenyl]urea (Compound 114)

General procedure: 1

Starting compound II: 2-Chloro-4-[(4-fluoro-2-aminophenyl)amino]-2'-methylbenzophenone Starting compound III: Ethyl Isocyanate Solvent for the reaction: Pyridine Purification: Chromatography using EtOAc/pentane 1:2 as eluant to give the title compound as an syrupy $^{13}$C NMR (CDCl$_3$): δ 197.2, 162.9, 159.6, 155.1, 150.2, 138.9, 137.8, 137.4,,137.2, 135.1, 133.6, 131.4, 131.1, 129.7, 128.4, 128.0, 127.9, 125.5, 124.7, 115.6, 111.8, 110.1, 109.8, 108.2, 107.9, 35.2, 20.5, 15.1

Example 15

1-Ethyl-3-[2-[3-chloro-4-(2-methylbenzoyl)-N-methyl-phenylamino]-5-fluoro-phenyl]urea (Compound 115)

General procedure: 1

Starting compound II: 4-(2-Amino-4-bromo-N-methyl-phenylamino)-2-chloro-2'-methylbenzophenone Purification: Chromatography using EtOAc/pentane 1:5 as eluant $^{13}$C NMR (CDCl$_3$): δ 197.6, 162.2, 154.8, 152.8, 139.4, .138.8, 137.1, 135.4, 133.9, 31.3, 130.9, 129.6, 129.0, 1Z8.5, 126.3, 125.5, 114.9, 111.1, 109.3, 107.1, 39.4, 34.9, 20.3, 14.8

Example 16

1-Ethyl-3-[5-bromo-2-[3-chloro-4-(4-n-butyl-2-methylbenzoyl)-phenylamino]phenyl]urea (Compound 116)

General procedure: 1

Starting compound II: 4-(2-Amino-4-bromophenylamino)-4'-n-butyl-2-chloro-2'-methylbenzophenone Starting compound III: Ethyl isocyanate Solvent for the reaction: Pyridine $^{13}$H NMR (DMSO-d$_6$): δ 8.36 (m, 1H), 8.27 (s, 1H), 7.94 (s, 1H), 7.24 (d, 1H), 7.2–7.0 (m, 5H), 6.86 (t, 1H), 6.69 (d, 1H), 6.58 (dd, 1H), 3.08 (m, 2H), 2.59 (t, 2H) 2.32 (s, 3H), 1.56 (m, 2H), 1.30 (m, 2H), 1.15–0.80 (m, 6H)

Example 17

1-Ethyl-3-[5-bromo-2-[3-chloro-4-(2,5-dimethylbenzoyl)-phenylamino]phenyl]urea (Compound 117)

General procedure: 1

Starting compound II: 4-(2-Amino-4-bromophenylamino)-2-chloro-2',5'-dimethylbenzophenone Starting compound III: Ethyl isocyanate Solvent for the reaction: Pyridine Purification: Crystallization from a mixture of 1,2-dichloroethane/hexane $^{13}$C NMR (DMSO-d$_6$): δ 195.5, 154.8, 150.3, 139.2, 138.1, 134.7, 133.6, 133.5, 133.4, 131.4, 131.0, 129.1, 127.8, 127.4, 126.5, 124.2, 121.9, 118.4, 115.1, 111.6, 33.9, 20.4, 19.4, 15.2

Example 18

1-Ethyl-3-[5-bromo-2-[3-chloro-4-(3-chloro-2-methylbenzoyl)-phenylamino]phenyl]urea (Compound 118)

General procedure: 1

Starting compound II: 4-(2-Amino-4-bromophenylamino)-2,3'-dichloro-2'-methylbenzophenone Starting compound III: Ethyl isocyanate Solvent for the reaction: Pyridine Purification: Crystallization from a mixture of 1,2-dichloroethane/hexane $^{13}$C NMR (DMSO-d$_6$): δ 193.8,; 154.6, 151.0, 142.3, 138.0, 134.5, 134.4, 134.1, 133.2, 130.7, 127.9, 127.2, 127.0, 126.5, 124.9, 124.1, 121.9, 118.6, 115.2, 111.5, 33.8, 16.6, 15.1

Example 19

1-Ethyl-3-[5-bromo-2-[3-chloro-4-(4-ethoxy-2-methylbenzoyl)-phenylamino]phenyl]urea (Compound 119)

General procedure: 1

Starting compound II: 4-(2-Amino-4-bromophenylamino)-2-chloro-4'-ethoxy-2'-methylbenzophenone Starting compound III: Ethyl isocyanate Solvent for the reaction: Pyridine Purification: Crystallization from a mixture of 1,2-dichloroethane/hexane $^{13}$C NMR (DMSO-d$_6$): δ 194.5, 160.8, 154.8, 149.6, 140.6, 138.0, 132.9, 132.5, 132.3, 130.6, 128.2, 127.8, 127.6, 124.2, 121.9, 118.2, 117.3, 114.7, 111.8, 111.1, 63.3, 33.9, 20.8, 15.2, 14.6

Example 20

1-Ethyl-3-[5-bromo-2-[3-ethoxy-4-(2-methylbenzoyl)-phenylamino]phenyl]urea (Compound 120)

General procedure: 1

Starting compound II: 4-(2-Amino-4-bromophenylamino)-2-ethoxy-2'-methylbenzophenone Starting compound III: Ethyl isocyanate Solvent for the reaction: Pyridine Purification: Crystallization from a mixture of 1,2-dichloroethane/hexane $^{13}$C NMR (DMSO-d$_6$): δ 195.2, 160.2, 154.7, 151.9, 143.1, 137.4, 134.2, 132.3, 129.9, 128.6, 128.3, 127.1, 126.3, 125.0, 124.1, 122.2, 118.0, 117.5, 106.6, 97.2, 62.9, 33.8, 19.2, 15.1, 13.5

Example 21

1-Ethyl-3-[1-bromo-2-[3-chloro-4-(4-chloro-2-methylbenzoyl)-phenylamino]phenyl]urea (Compound 121)

General procedure: 1

Starting compound II: 4-(2-Amino-4-bromophenylamino)-2,4'-dichloro-2'-methylbenzophenone Starting compound III: Ethyl isocyanate Solvent for the reaction: Pyridine Purification: Crystallization from a mixture of 1,2-dichloroethane/hexane $^{13}$C NMR (DMSO-d$_6$): δ 194.1, 154.6, 150.6, 139.0, 138.0, 135.1, 133.6, 133.5, 130.6, 130.4, 127.8, 127.2, 125.9, :125.6, 124.1, 121.8, 118.4, 114.9, 111.6, 45.0, 33.8, 19.4, 15.1

Example 22

1-Ethyl-3-[5-bromo-2-[3-chloro-4-(2,3-dimethylbenzoyl)-phenylamino]phenyl]urea (Compound 122)

General procedure: 1

Starting compound II: 4-(2-Amino-4-bromophenylamino)-2-chloro-2',3'-dimethylbenzophenone Starting compound III: Ethyl isocyanate Solvent for the reaction: Pyridine Purification: Crystallization from a mixture of 1,2-dichloroethane/hexane $^{13}$C NMR (DMSO-d$_6$). δ 195.6, 154.6, 150.5, 140.3, 138.0, 137.4, 134.2, 134.0, 133.7, 131.5, 127.8, 127.2, 126.0, 125.6, 125.1, 124.1, 121.8, 118.4, 115.1, 111.4, 33.8, 19.6, 16.0, 15.1

Example 23

1-Ethyl-3-[5-bromo-2-[3-fluoro-4-(4-methoxy-2-methylbenzoyl)-phenylamino]phenyl]urea (Compound 123)

General procedure: 1

Starting compound II: 4-(2-Amino-4-bromophenylamino)-2-fluoro-4'-methoxy-2'-methylbenzophenone Starting compound III: Ethyl isocyanate Solvent for the reaction: Pyridine Purification: Crystallization from a mixture of 1,2-dichloroethane/hexane $^{13}$C NMR (DMSO-d$_6$): δ 192.0, 162.3, 160.8, 154.8, 152.2, 138.9, 138.0, 133.1, 132.3, 131.1, 127.8, 127.6, 124.2, 122.0, 118.4, 116.6, 116.4, 110.7, 109.8, 100.1, 55.3, 33.9, 20.2, 15.2

Example 24

1-Ethyl-3-[5-bromo-2-[3-chloro-4-(2,4,5-trimethylbenzoyl)-phenylamino]phenyl]urea (Compound 124)

General procedure: 1

Starting compound II: 4'-(2-Amino-4-bromophenylamino)-2'-chloro-2,4,5-trimethylbenzophenone Starting compound III: Ethyl isocyanate Solvent for the reaction: Pyridine Purification: Crystallization from a mixture of 1,2-dichloroethane/hexane $^{13}$C NMR (DMSO-d$_6$): δ195.2, 154.7, 149.9, 139.6, 137.9, 136.4, 134.2, 133.2, 133.0, 132.4, 130.3, 127.6, 127.5, 127.1, 124.1, 121.8, 118.2, 114.8, 111.6, 33.8, 19.4, 19.2, 18.6, 15.1

Example 25

1-Ethyl-3-[5-bromo-2-[3-chloro-4-(4-fluoro-2-methylbenzoyl)-phenylamino]phenyl]urea (Compound 125)

General procedure: 1

Starting compound II: 4-(2-Amino-4-bromophenylamino)-2-chloro-4'-fluoro-2'-methylbenzophenone Starting compound III: Ethyl isocyanate Solvent for the reaction: Pyridine Purification: Crystallization from a mixture of 1,2-dichloroethane/hexane $^{13}$C NMR (DMSO-d$_6$): δ 194.1, 162.9, 154.6, 150.3, 140.4, 138.0, 135.6, 133.3, 131.6, 127.7, 127.3, 126.4, 124.1, 121.8, 118.3, 117.7, 114.8, 112.4, 111.6, 33.8, 19.8, 15.1

Example 26

1-Ethyl-3-[5-bromo-2-[3-fluoro-4-(2-methylbenzoyl)-phenylamino]phenyl]urea (Compound 126)

General procedure: 1

Starting compound II: 4-(2-Amino-4-bromophenylamino)-2-fluoro-2'-methylbenzophenone Starting compound III: Ethyl isocyanate Solvent for the reaction: Pyridine Purification: Crystallization from a mixture of 1,2-dichloroethane/hexane $^{13}$C NMR (DMSO-d$_6$): δ192.9, 163.0, 154.8, 153.0, 140.7, 138.0, 135.0, 133.3, 130.6, 129.9, 128.0, 127.2, 125.5, 124.2, 122.0, 118.6, 115.5, 109.9, 100.1, 33.9, 19.3, 15.2

Example 27

Tablet Containing Compound 102

| | |
|---|---|
| Compound 102 (active substance) | 50 mg |
| Lactose | 125 mg |
| Starch | 12 mg |
| Methyl cellulose | 2 mg |
| Sodium carboxymethyl cellulose | 10 mg |
| Magnesium stearate | 1 mg |

The active substance, lactose and starch are mixed to a homogeneous state in a suitable mixer and moistened with a 5 per cent aqueous solution of methyl cellulose 15 cps. The mixing is continued until granules are formed. If necessary, the wet granulation is passed through a suitable screen and dried to a water content of less than 1% in a suitable drier, e.g. fluid bed or drying oven. The dried granules are passed through a 1 mm screen and mixed to a homogeneous state with sodium carboxymethyl cellulose. Magnesium stearate is added, and the mixing is continued for a short period of time. Tablets with a weight of 200 mg are produced from the granulation by means of a suitable tabletting machine.

Example 28

Formulation for Injection Containing Compound 102

| | |
|---|---|
| Compound 102 (active substance) | 1% |
| Sodium chloride | q.s. |
| Ethanol | 10% |
| Water for injection to make | 100% |

The active substance is dissolved in ethanol (10%) then water for injection made isotonic with sodium chloride is added to make 100%. The mixture is filled into ampoules and sterilized.

Example 29

Cream Formulation Containing Compound 101

Compound 101 (10 g) was dissolved in Octyldodecyl myristate (250 g) to form Part A. Methylparaben (1 g) and propylparaben (0.2 g) were dissolved in phenoxyethanol (6 g) and mixed with a 0.025 M Phosphate buffer pH=7.5 (632,8 g) to form Part B. Cetostearyl alcohol (50 g) and ARLACEL 165® (50 g) was melted in a vessel at 70° to 80° C. Part A was added and heated to 60–70° C. The aqueous phase was likewise heated to 60–70° C. and slowly added to the melted oil phase under high speed stirring. The homogenized components were cooled to room temperature.

What is claimed is:

1. A compound of the formula I

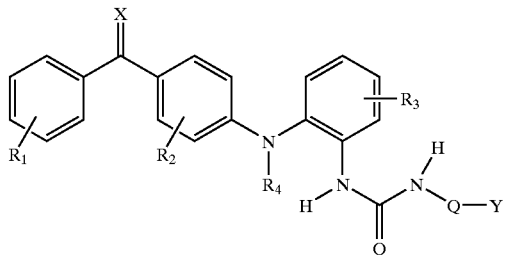

I wherein $R_1$ independently represents one or more, same or different substituents selected from the group consisting of halogen, hydroxy, mercapto, trifluoromethyl, amino, $(C_1-C_3)$alkyl, $(C_2-C_3)$olefinic group, $(C_1-C_3)$alkoxy, $(C_1-C_3)$alkylthio, $(C_1-C_6)$alkylamino, $(C_1-C_3)$ alkoxycarbonyl, cyano, carbamoyl, phenyl and nitro, provided that when $R_1$ represents one substituent, it is in the ortho position, and when $R_1$ represents more than one substituent, at least one $R_1$ substituent is in the ortho position;

$R_2$ is one substituent in the ortho position, said substituent being selected from the group consisting of halogen, hydroxy, mercapto, trifluoromethyl, amino, $(C_1-C_3)$ alkyl, $(C_2-C_3)$olefinic group, $(C_1-C_3)$alkoxy, $(C_1-C_3)$ alkylthio, $(C_1-C_6)$alkylamino, $(C_1-C_3)$alkoxycarbonyl, cyano, carbamoyl, phenyl and nitro;

$R_3$ represents hydrogen, halogen, hydroxy, mercapto, trifluoromethyl, amino, $(C_1-C_3)$alkyl, $(C_2-C_3)$olefinic group, $(C_1-C_3)$alkoxy, $(C_1-C_3)$alkylthio, $(C_1-C_6)$ alkylamino, $(C_1-C_3)$alkoxycarbonyl, phenyl, cyano, carboxy, or carbamoyl;

$R_4$ represents hydrogen, $(C_1-C_3)$alkyl, or allyl;

Q represents a bond, —$SO_2$—, or —$C(R_6)(R_7)(-O-C=O)$—, in which formula $R_6$ and $R_7$ independently represent hydrogen, trifluoromethyl, or $(C_1-C_4)$alkyl;

Y represents $(C_1-C_{15})$alkyl, $(C_2-C_{15})$olefinic group, $(C_3-C_{10})$carbocyclic group, or phenyl, any of which is optionally substituted by one or more, same or different substituents represented by the formula $R_5$; or Y represents a group of formula —$(Z-O)_n$—Z, where Z is a $(C_1-C_3)$alkyl and n is an integer >1, and no continuous linear sequence of atoms in the group Y exceeds 15;

$R_5$ represents halogen, hydroxy, mercapto, trifluoromethyl, $(C_1-C_4)$alkyl, amino, $(C_1-C_3)$alkoxy, $(C_1-C_3)$alkylthio, $(C_1-C_6)$alkylamino, $(C_1-C_3)$ alkoxycarbonyl, cyano, azido, nitro, —COOH, —$CONH_2$, —CONHR', or —CONRR' wherein R and R' stands for $(C_1-C_3)$alkyl;

X represents oxygen or sulphur, or a pharmaceutically acceptable salt thereof, or a hydrate or solvate thereof.

2. A compound according to claim 1 wherein independently $R_1$ represents one or more, same or different substituents selected from the group consisting of fluoro, chloro, bromo, hydroxy, trifluoromethyl, amino, $(C_1-C_2)$alkyl, $(C_2-C_3)$alkenyl, $(C_1-C_3)$alkoxy, $(C_1-C_3)$ alkoxycarbonyl, or cyano, $R_2$ represents one or more, same or different substituents selected from the group consisting of fluoro, chloro, bromo, hydroxy, trifluoromethyl, amino, $(C_1-C_2)$alkyl, $(C_2-C_3)$alkenyl, $(C_1-C_3)$alkoxy, $R_3$ represents one or more, same or different substituents selected from the group consisting of hydrogen, fluoro, chloro, bromo, hydroxy, trifluoromethyl, $(C_1-C_3)$alkyl, $(C_2-C_3)$alkenyl, $(C_1-C_3)$alkoxy, $(C_1-C_3)$ alkoxycarbonyl, cyano, or carboxy, $R_4$ represents hydrogen, $(C_1-C_2)$alkyl, or allyl, X represents oxygen, Q represents a bond or —$SO_2$—, Y represents $(C_1-C_6)$alkyl; $(C_2-C_6)$alkenyl; $(C_3-C_6)$ cycloalkyl; $(C_5-C_8)$cycloalkene group;, or phenyl; any of which is optionally substituted by one or more, same or different substituents selected from the group consisting of the formula $R_5$, $R_5$ representing fluoro, chloro, bromo, hydroxy, amino, $(C_1-C_2)$alkoxy, $(C_1-C_4)$alkylamino, $(C_1-C_3)$alkoxycarbonyl, cyano, azido, —COOH, —$CONH_2$, —CONHR', or —CONR'R' wherein R' represents $(C_1-C_2)$alkyl.

3. A compound according to claim 1 or 2 wherein $R_1$ represents one or more, same or different substituents selected from the group consisting of fluoro, chloro, bromo, hydroxy, methyl, or methoxy.

4. A compound according to claim 1, wherein $R_1$ is methyl and $R_2$ is Cl.

5. A compound according to claim 1 selected from the group consisting of

1-Cyclohexyl-3-[2-[3-chloro-4-(2-methylbenzoyl)-phenylamino]phenyl]urea (Compound 101), 1-Ethyl-3-[2-[3-chloro-4-(2-methylbenzoyl)-phenylamino] phenyl]urea (Compound 102), 1-[2-[3-Chloro-4-(2-methylbenzoyl)-phenylamino]phenyl]-3-phenylurea (Compound 103), 1-Butyl-3-[2-[3-chloro-4-(2-methylbenzoyl)-phenylamino] phenyl]urea (Compound 104), 1-[2-[3-Chloro-4-(2-methylbenzoyl)-phenylamino]phenyl]-3-iso-propylurea (Compound 108), 1-[2-[3-Chloro-4-(2-methylbenzoyl)-phenylamino]phenyl]-3-propylurea (Compound 109), 1-Methyl-3-[2-[3-chloro-4-(2-methylbenzoyl)-phenylamino]phenyl]urea (Compound 110), 1-Ethyl-3-[5-bromo-2-[3-chloro-4-(2-methylbenzoyl)-phenylamino]phenyl]urea (Compound 112), 1-Ethyl-3-[2-[3-chloro-4-(2-methylbenzoyl)-phenylamino]-5-fluoro-phenyl]urea (Compound 114), 1-Ethyl-3-[5-bromo-2-[3-chloro-4-(2,5-dimethylbenzoyl)-phenylamino]phenyl]urea (Compound 117), 1-Ethyl-3-[5-bromo-2-[3-chloro-4-(4-chloro-2-methylbenzoyl)-phenylamino]phenyl]urea (Compound 121), 1-Ethyl-3-[5-bromo-2-[3-fluoro-4-(4-methoxy-2-methylbenzoyl)-phenylamino]phenyl]urea (Compound 123), 1-Ethyl-3-[5-bromo-2-[3-chloro-4-(2,4,5-trimethylbenzoyl)-phenylamino]phenyl]urea (Compound 124), 1-Ethyl-3-[5-bromo-2-[3-chloro-4-(4-fluoro-2-methylbenzoyl)-phenylamino]phenyl]urea (Compound 125), 1-Ethyl-3-[5-bromo-2-[3-fluoro-4-(2-methylbenzoyl)-phenylamino]phenyl]urea (Compound 126), and salts thereof with pharmaceutically acceptable acids, hydrates and solvates.

6. A pharmaceutical composition containing as an active ingredient a compound according to claim 1 together with a pharmaceutically acceptable carrier and optionally together with a second active ingredient optionally selected from the group consisting of glucocorticoids, vitamins D's, anti-histamines, platelet activating factor (PAF) antagonists, anticolinergic agents, methyl xanthines, β-adrenergic agents, salicylates, indomethacin, flufenamate, naproxen, timegadine, gold salts, penicillamine, serum cholesterol-reducing agents, retinoids, zinc salts, and salicylazosulfapyridin (Salazopyrin).

7. A method for the treatment and/or prophylaxis of asthma, allergy, arthritis, including rheumatoid arthritis and spondyloarthritis, gout, atherosclerosis, chronic inflammatory bowel disease (Crohn's disease), proliferative and inflammatory skin disorders, such as psoriasis, atopic dermatitis, uveitis, septic shock, AIDS, osteoporosis and acne, which comprises administering to a patient suffering from at least one of said diseases an effective amount of one or more compounds according to claim 1 as an active ingredient alone, or optionally together with a pharmaceutically acceptable carrier, and, optionally, a second active ingredient optionally selected from the group consisting of glucocorticoids, vitamin D's, anti-histamines, platelet activating factor (PAF) antagonists, anticolinergic agents, methyl xanthines, β-adrenergic agents, salicylates, indomethacin, flufenamate, naproxen, timegadine, gold salts, penicillamine, serum cholesterol-reducing agents, retinoids, zinc salts, and salicylazosulfapyridin (Salazopyrin).

8. A method of treatment according to claim 7, wherein a suitable dose of a compound of formula I of from 0.1 to 200 mg/kg bodyweight is administered one or more times daily.

9. A method of treatment according to claim 7, wherein a suitable dose of a compound of formula I of from 0.2 to 50 mg/kg bodyweight is administered one or more times daily.

10. A method for inhibiting interleukin 1β or tumour necrosis factor α secretion, which comprises administering to a mammal or patient in need thereof an effective amount of one or more compounds according to claim 1.

11. A method of treatment according to claim 10, wherein interleukin 1β secretion is inhibited.

12. A method of treatment according to claim 10, wherein tumour necrosis factor α secretion is inhibited.

13. A method of treatment according to claim 10, wherein the compound is administered to the mammal or patient in a dosage range of from 0.1 to 200 mg/kg bodyweight one or more times daily.

14. A method of treatment according to claim 10, wherein the compound is administered to the mammal or patient in a dosage range of from 0.2 to 50 mg/kg bodyweight one or more times daily.

* * * * *